United States Patent [19]

Windawi

[11] 4,421,938

[45] Dec. 20, 1983

[54] PREPARATION OF ALDEHYDES

[75] Inventor: Hassan Windawi, Arlington Heights, Ill.

[73] Assignee: UOP Inc., Des Plaines, Ill.

[21] Appl. No.: 365,718

[22] Filed: Apr. 5, 1982

[51] Int. Cl.$^3$ .............................................. C07C 45/29
[52] U.S. Cl. ................................. 568/474; 568/471; 568/472
[58] Field of Search ........................ 568/471, 472, 474

[56] References Cited

U.S. PATENT DOCUMENTS

| | | | |
|---|---|---|---|
| 1,636,952 | 7/1927 | Graver | 568/471 |
| 2,086,702 | 7/1937 | Dreyfus | 568/471 |
| 2,439,880 | 4/1949 | Arnold | 568/474 |
| 2,849,493 | 8/1958 | Shelton et al. | 568/474 |
| 3,852,361 | 12/1974 | Haas et al. | 568/474 |
| 4,218,401 | 8/1980 | Wymore | 568/471 |
| 4,355,187 | 10/1982 | Baltes et al. | 568/474 |

FOREIGN PATENT DOCUMENTS 2450931 4/1975 Fed. Rep. of Germany ...... 568/474

OTHER PUBLICATIONS

Mann et al., "Ind. Eng. Chem. Process Des. Develop., vol. 9, No. 1, (1970).

*Primary Examiner*—Werren B. Lone
*Attorney, Agent, or Firm*—James R. Hoatson, Jr.; Raymond H. Nelson; William H. Page, II

[57] ABSTRACT

Alcohols such as those containing from about 1 to about 10 carbon atoms may be converted to aldehydes by treating the alcohols with an oxygen-containing gas such as air or oxygen in the presence of a catalyst comprising at least two oxides of metals selected from the group consisting of molybdenum, tungsten, cobalt, nickel, manganese, iron and chromium, at least one of said oxides being molybdenum oxide or tungsten oxide composited on a high surface area support. The conversion reaction may be effected at a temperature ranging from about 200° to about 400° C. and a pressure in the range of from about atmospheric to about 50 atmospheres. By employing this particular catalyst, good conversion rates and high selectivity to the aldehydes will be obtained.

12 Claims, No Drawings

PREPARATION OF ALDEHYDES

BACKGROUND OF THE INVENTION

Aldehydes comprise important chemical compounds which are useful for a variety of purposes. One source of various aldehydes comprises alcohols, the aldehydes being prepared by the oxidative dehydrogenation of the corresponding alcohols. When this type of process is employed, the oxidative dehydrogenation has been effected in the presence of catalysts such as silver catalysts, platinum black, etc. The process conditions which have been used to effect this oxidation have been in the range of from about 450° to about 550° C. The by-products which have been obtained from this reaction usually include the corresponding acids, esters, ethers, etc., the amount of said by-products being dependent to some extent upon the operating parameters employed in the reaction. In addition to the oxidative dehydrogenation of the alcohols, other methods of obtaining aldehydes have included the direct oxidation of paraffins, the hydration of alkynes utilized, mercuric sulfate or ferric sulfate catalysts, etc.

As was previously set forth, aldehydes are important articles of commerce as, for example, acetaldehyde which is used in the preparation of acetic acid, acetic anhydride, chloral, as an intermediate for drugs, perfumes, photographic agents, in phenol and urea condensation products, etc. Likewise, propionaldehyde is used in the manufacture of polyvinyl acetals and other types of plastics, in the synthesis of rubber chemicals, as a disinfectant or preservative etc; isovaleraldehyde is used in flavoring compounds, perfumes, pharmaceuticals, synthetic resins, rubber accelerators, etc.

As will hereinafter be shown in greater detail, it has now been discovered that alcohols may be converted to corresponding aldehydes in an oxidation type reaction involving the use of catalytic composition of matter which possesses favorable characteristics of activity, selectivity, stability, etc.

BRIEF DESCRIPTION OF THE INVENTION

This invention relates to a process for the conversion of alcohols to aldehydes. More specifically, the invention is concerned with a process for the oxidation of an alcohol to form the corresponding aldehyde in which a catalytic composition of matter is employed which will enable the conversion process to be effected under relatively mild reaction conditions.

As hereinbefore set forth, it has now been discovered that certain catalytic compositions of matter, of the type hereinafter set forth in greater detail, may be employed in a conversion reaction which involves the treatment of an alcohol with an oxygen-containing gas whereby said alcohol is converted to the corresponding aldehyde in a relatively high conversion per pass and selectivity to the desired product. The catalysts which are employed for this reaction will comprise a mixture of at least two oxides composited on a solid support, said catalysts possessing the desirable characteristics which include high activity, high selectivity, high stability and relatively low cost when compared to previously used catalysts which employ the noble metals such as silver, platinum, palladium, etc.

It is therefore an object of this invention to provide a process for the conversion of an alcohol to an aldehyde.

A further object of this invention is to provide a relatively inexpensive process for conversion of an alcohol to an aldehyde by employing certain catalytic compositions of matter.

In one aspect, an embodiment of this invention resides in a process for the conversion of an alcohol to an aldehyde which comprises treating said alcohol with an oxygen-containing gas at treating conditions in the presence of a catalyst comprising at least two oxides of metals selected from the group consisting of molybdenum, tungsten, cobalt, nickel, manganese, iron and chromium, one of said oxides being molybdenum oxide or tungsten oxide, composited on a high surface area support, and recovering the resultant aldehyde.

A specific embodiment of this invention is found in a process for the conversion of ethanol to acetaldehyde which comprises treating said ethanol with air in the presence of a catalyst comprising molybdenum oxide, nickel oxide, and manganese oxide composited on gamma-alumina at a temperature in the range of from about 200° to about 400° C., a pressure in the range of from about atmospheric to about 50 atmospheres and a liquid hourly space velocity in the range of from about 1 to about 10, and recovering the resulting acetaldehyde.

Other objects and embodiments will be found in the following further detailed description of the present invention.

DETAILED DESCRIPTION OF THE INVENTION

As hereinbefore set forth, the present invention is concerned with a process for converting an alcohol to the corresponding aldehyde utilizing a particular catalytic composition of matter whereby a high rate of conversion is obtained with a corresponding high selectivity to the desired product, namely, the aldehyde. By utilizing the catalyst employed in the process of the present invention, it is possible to obtain the desired product in a relatively more inexpensive manner inasmuch as it is possible to effect the conversion reaction using operating parameters of temperature and pressure which are less severe than those which have heretofore been employed as well as utilizing a catalyst which is less expensive to manufacture or produce.

The conversion of the alcohol to the corresponding aldehyde will be effected under operating conditions which will include a temperature in the range of from about 200° to about 400° C. and a pressure which may range from atmospheric up to about 50 atmospheres or more while employing liquid hourly space velocities which may range from about 1 to about 10 or more. In the preferred embodiment of the invention, the operating temperatures will range from about 225° up to about 300° C., while operating the process at atmospheric pressure. Inasmuch as the preferred operating parameters are relatively mild in nature, it is possible to utilize apparatus which, in itself, may be relatively inexpensive, the use of atmospheric pressure obviating the necessity for pressure-resistant articles of equipment such as autoclaves, etc.

The alcohols which are converted to the corresponding aldehydes may comprise those containing from 1 to about 10 carbon atoms in the aliphatic chain, said chain itself being straight or branched in configuration. Some specific examples of alcohols which may be converted to the corresponding aldehydes will include methanol, ethanol, n-propanol, isopropanol, n-butanol, sec-butanol, t-butanol, n-pentanol, sec-pentanol, the corresponding isomeric hexanes, heptanes, octanes, nonanes, decanes, etc. The conversion of these alcohols to the corresponding aldehydes is effected by treating the alcohol with an oxygen-containing gas which may comprise oxygen, air, or mixtures of oxygen with inert gases such as nitrogen, argon, helium, etc. in the presence of a catalytic composition of matter which comprises at least two metal oxides composited on a solid support.

The catalytic composition of matter which may be used to effect the desired conversion of the alcohol to the aldehyde comprises at least two oxides of metals selected from the group consisting of molybdenum, tungsten, cobalt, nickel, manganese, iron, chromium, at least one of said oxides being molybdenum oxide or tungsten oxide, composited on a high surface area support. The high surface area support, in the preferred embodiment of the invention, comprises an inorganic oxide which possesses a surface area in the range of from about 1 to about 500 m$^2$/g. Some specific inorganic oxide supports which may be employed as the base for the mixture of metal oxides will include various aluminas such as gamma-alumina, eta-alumina, theta-alumina, silica, zeolites, mixtures of inorganic oxides such as alumina-silica, alumina-zirconia, alumina-magnesia, alumina-zirconia-silica, etc.

The aforementioned oxides of the metals set forth in the aforementioned class will be composited on the solid support in a total amount which may range from about 5% to about 25%. Generally speaking, the oxide of molybdenum or tungsten which comprises an essential component of the catalytic composition of matter will be present in an amount in the range of from about 3% to about 20%, the remainder of the total metal oxide comprising either one or more of the aforesaid metal oxides.

Some specific examples of the catalytic components which may be employed to effect the conversion of alcohols to corresponding aldehydes will include molybdenum oxide, nickel oxide and manganese oxide composited on gamma-alumina, tungsten oxide, nickel oxide and manganese oxide composited on gamma alumina, molybdenum oxide, cobalt oxide and manganese oxide composited on gamma-alumina, molybdenum oxide, chromium oxide and nickel oxide composited in gamma-alumina, tungsten oxide, manganese oxide and ferric oxide composited on gamma-alumina, etc. It is to be understood that the aforementioned catalysts are only representative of the type of composites which may be employed in the conversion process and that the present invention it not necessarily limited thereto.

The process of this invention may be effected in any suitable manner and may comprise either a batch or continuous type operation. For example, when a batch type operation is used, the quantity of the catalyst comprising at least two metal oxides of the type hereinbefore set forth, at least one of the metal oxides being molybdenum oxide or tungsten oxide composited on a solid support, is placed in an appropriate apparatus. This apparatus may comprise a tube reactor, a pressure-resistant vessel such as an autoclave, etc. The alcohol which is to undergo conversion is charged to the reactor along with the oxygen-containing gas. One embodiment of the invention contemplates that the alcohol and oxygen-containing gas such as air may be charged to the reaction vessel as a mixture such as air saturated with methanol, ethanol, etc. or, if so desired, the alcohol and oxygen-containing gas may be charged to the reactor through separate means. The reactor may be pre-heated to the desired operating temperature prior to receiving the alcohol and oxygen-containing gas or, if so desired, the charge stock may be added to the reactor which is subsequently heated to the desired operating temperature. After the alcohol and oxygen-containing gas have been in contact with the catalyst for a pre-determined period of time which may range from about 0.5 up to about 4 hours or more in duration, the reaction product is recovered and subjected to conventional means of separation such as fractional distillation, etc. whereby the desired aldehyde is separated from any side reaction products which may have formed such as acids, ethers, esters, etc., and recovered.

It is also contemplated within the scope of this invention that the conversion process whereby an alcohol is converted to an aldehyde may be effected in a continuous manner of operation. When such a type of operation is employed, a catalyst of the type hereinbefore described is placed in an appropriate apparatus which is maintained at the proper operating conditions of temperature and pressure. The alcoholic feedstock is continuously charged to the reactor as is the oxygen-containing gas. As in the description of the batch type operation, the oxygen-containing gas and alcohol may be charged to the reactor as a mixture in a single stream or, alternatively, the alcohol and oxygen-containing gas may be admitted to the reactor through separate means. After passage through the reactor for the desired operational time, the reactor effluent is continuously withdrawn and again subjected to the conventional means of separation whereby the desired aldehyde product is separated and recovered, any unreacted alcohol which is recovered from the separation being recycled to the reactor to form a portion of the feedstock.

Inasmuch as the catalyst which is used to effect the reaction is solid in nature, the continuous type of operation may be effected in various ways. One way of effecting the reaction is to employ the catalyst as a fixed bed in the reactor while passing the alcohol and oxygen-containing gas over the catalyst in either an upward or downward flow. Another method of effecting the desired conversion reaction is to employ a moving bed type of operation in which the catalyst moves through the reactor while the alcohol and oxygen-containing gas contact the catalyst in either a concurrent or countercurrent flow. Yet another method of effecting a continuous type of operation comprises the slurry type in which the catalyst is carried into the reactor as a slurry in the alcohol feedstock and is continuously removed along with the reaction product.

The conversion of the alcohols containing from 1 to 10 carbon atoms will result in obtaining useful chemical compounds such as formaldehyde, acetaldehyde, propionaldehyde, butyraldehyde, valeraldehyde, caproaldehyde, heptylaldehyde (oenanthole), caprylaldehyde, pelargonaldehyde, carpaldehyde, etc.

The following examples are given for purposes of illustrating the process of the present invention. However, it is to be understood that these examples are given merely for purposes of illustration and that the present process is not necessarily limited thereto.

EXAMPLE I

In this example, 1 gram of a catalyst composite comprising 9 wt. % molybdenum, 2.5 wt. % nickel, and 2.5 wt. % manganese (the wt. % being based on the metals of the aforesaid material), composited on a gamma-alumina base, was placed in a tube reactor, the catalyst having been crushed to a mesh size of from 35 to 40.

Following this, a stream of air saturated with ethanol at room temperature was passed over the catalyst in the reactor at a liquid hourly space velocity of 1, said reactor being maintained at a temperature of 250° C. The effluent from the reactor was condensed on a dry ice bed and analyzed upon recovery by means of gas chromatography. The analysis determined that there had been a 50% conversion of the ethanol with an 85% mole fraction selectivity to acetaldehyde, the remainder of the product comprising a mixture of ethyl acetate, diethyl ether, acetic acid and methanol.

EXAMPLE II

In this example, the above experiment was repeated by passing a stream of air saturated with ethanol, in which the ethanol vapor pressure was 54 mm, over 1 gram of the catalyst at a liquid hourly space velocity of 1, the reactor and catalyst being maintained at a temperature of 300° C. Analysis of the effluent which was recovered from the reactor showed that there had been only a 35% selectivity to acetaldehyde.

EXAMPLE III

To illustrate the effect of space velocity, the experiment was repeated utilizing a catalyst similar to that set forth in the above examples. The feedstock comprising a stream of air saturated with a sufficient amount of ethanol at room temperature to provide an ethanol vapor pressure of 54 mm was passed over the catalyst which was maintained at a temperature of 250° C. at a liquid hourly space velocity of 1.5. Analysis of the effluent which was recovered showed that the conversion of the ethanol was only 30%, however, the selectivity was 100% acetaldehyde.

When the temperature of the reaction was increased to 300° C., using a liquid hourly space velocity of 1.5, the selectivity to acetaldehyde was reduced to 49%.

EXAMPLE IV

When other alcohols such as methanol, propanol, and butanol are subjected to a conversion reacting utilizing other conversion catalysts such as tungsten oxide, nickel oxide and manganese oxide composited on gamma-alumina or a mixture of molybdenum oxide, copper oxide and manganese oxide composited on gamma-alumina at a reaction temperature of 250° C. and a liquid hourly space velocity of 1.5, the aforesaid alcohols may be converted to the corresponding aldehydes such as formaldehyde, propionaldehyde and butyraldehyde, respectively.

I claim as my invention:

1. In a process for the conversion of an aliphatic alcohol containing from 1 to about 10 carbon atoms in the aliphatic chain to the corresponding aldehyde by reaction of the alcohol with an oxygen-containing gas at a temperature in the range of from about 200° C. to about 400° C., a pressure in the range of from about atmospheric to about 50 atmospheres and a liquid hourly space velocity in the range of from about 1 to about 10, the improvement which comprises reacting said alcohol and gas in the presence of a catalyst comprising at least two oxides of metals selected from the group consisting of molybdenum, tungsten, cobalt, nickel, manganese, iron and chromium, one of said oxides being molybdenum oxide or tungsten oxide, composited on a high surface area support selected from the group consisting of gamma-alumina, eta-alumina, theta-alumina, silica, zeolites, alumina-silica, alumina-zirconia, alumina-magnesia and alumina-zirconium-silica.

2. The process as set forth in claim 1 in which said oxygen-containing gas is oxygen.

3. The process as set forth in claim 1 in which said oxygen-containing gas is air.

4. The process as set forth in claim 1 in which said high surface area support is an alumina.

5. The process as set forth in claim 3 in which said alumina is gamma-alumina.

6. The process as set forth in claim 1 in which said catalyst comprises molybdenum oxide, nickel oxide and manganese oxide composited on gamma-alumina.

7. The process as set forth in claim 1 in which said catalyst comprises tungsten oxide, nickel oxide and manganese oxide composited on gamma-alumina.

8. The process as set forth in claim 1 in which said catalyst comprises molybdenum oxide, cobalt oxide and manganese oxide composited on gamma-alumina.

9. The process as set forth in claim 1 in which said alcohol is ethanol and said aldehyde is acetaldehyde.

10. The process as set forth in claim 1 in which said alcohol is propanol and said aldehyde is propionaldehyde.

11. The process as set forth in claim 1 in which said alcohol is methanol and said aldehyde is formaldehyde.

12. The process as set forth in claim 1 in which said alcohol is butanol and said aldehyde is butyraldehyde.

* * * * *